United States Patent
Huang et al.

(10) Patent No.: US 6,575,043 B1
(45) Date of Patent: Jun. 10, 2003

(54) METHOD AND APPARATUS FOR CHARACTERIZING FLOWS BASED ON ATTENUATION OF IN-WALL PROPAGATING WAVE MODES

(75) Inventors: Songming Huang, Hardwick (GB); Yan Kuhn de Chizelle, Girton (GB)

(73) Assignee: Schlumberger Technology Corporation, Ridgefield, CT (US)

(*) Notice: Subject to any disclaimer, the term of this patent is extended or adjusted under 35 U.S.C. 154(b) by 0 days.

(21) Appl. No.: 09/419,825

(22) Filed: Oct. 19, 1999

(30) Foreign Application Priority Data

Oct. 30, 1998 (GB) .............................. 9823675

(51) Int. Cl.$^7$ .............................. G01F 1/66; G01F 1/20

(52) U.S. Cl. .................................. 73/861.25; 73/861.18

(58) Field of Search .............................. 73/861–861.25, 73/861.28, 861.26

(56) References Cited

U.S. PATENT DOCUMENTS

| | | | | |
|---|---|---|---|---|
| 4,144,754 A | * | 3/1979 | Pitts et al. ................. | 73/861.02 |
| 4,378,168 A | * | 3/1983 | Kuisma et al. ............. | 374/28 |
| 4,524,621 A | * | 6/1985 | Yamanaka .................. | 73/597 |
| 4,735,097 A | * | 4/1988 | Lynnworth ................. | 73/290 V |
| 4,838,127 A | | 6/1989 | Herremans et al. | |
| 4,881,208 A | * | 11/1989 | Liu ........................... | 181/105 |
| 5,046,500 A | * | 9/1991 | Fehr .......................... | 600/455 |
| 5,235,235 A | * | 8/1993 | Martin et al. ............... | 310/313 B |
| 5,406,849 A | * | 4/1995 | Drescher-Krasicka et al. ........................ | 73/588 |
| 5,415,048 A | | 5/1995 | Diatschenko et al. | |
| 5,533,408 A | * | 7/1996 | Oldenziel et al. .......... | 73/861.06 |

FOREIGN PATENT DOCUMENTS

EP     0 212 470 A2     3/1987

OTHER PUBLICATIONS

Dukler, A. E. and Hubbard, M. G., A Model for Gas–Liquid Slug Flow in Horizontal and Near Horizontal Tubes, Ind. Eng. Chem. Fundam. vol. 14, No. 4, 1975, pp. 337–347.

Nicholson, M. K., Aziz, K. and Gregory, G. A., Intermittent Two Phase Flow in Horizontal Pipes: Predictive Models Canadian Journal of Chem. Eng., vol. 56, 1978, pp. 653–663.

Monkhouse, R. S. C., Wilcox, P. D. and Cawley, P., Flexible interdigital PVDF transducers for the generation of Lamb waves in structures, Ultrasonics, 35, 1997, pp. 489–498.

* cited by examiner

*Primary Examiner*—Hezron Williams
*Assistant Examiner*—Lilybett Martir
(74) *Attorney, Agent, or Firm*—William L. Wang; William B. Batzer; John J. Ryberg (57) ABSTRACT

Methods and apparatus are described that characterize flows within a conduit by generating acoustic waves, and receiving acoustic energy representing at least one in-wall leaky acoustic wave mode. Attenuation of acoustic energy that has entirely propagated within the wall of the conduit is measured and evaluated in order to derive parameters relating to the fluid or fluids flowing in the conduit. The wave modes described include bulk waves and lamb waves and propagate in axial and circumferential directions.

19 Claims, 11 Drawing Sheets

METHOD AND APPARATUS FOR CHARACTERIZING FLOWS BASED ON ATTENUATION OF IN-WALL PROPAGATING WAVE MODES

BACKGROUND OF THE INVENTION

The oil industry is increasingly demanding multi-phase flow-meters for well testing and monitoring. A multi-phase flow-meter for such applications is required to measure the flow rates of liquid (oil and water) and gas in a oil well tubulars, such as production pipelines, flowlines, risers etc. In order to determine flow rates of multi-phase flows, it is generally necessary to measure the velocities and the hold-ups of the liquid and gas phases. The flow velocity is the velocity at which the phase, i.e., liquid or gas, travels measured in distance over time. The holdup of a phase is the fraction of the cross-section of the total flow occupied by the phase in question. The holdup is usually expressed in per cent. With a known given cross-section of the pipe, measured holdup and velocity, the flow rate of a phase can be calculated as the product of those three parameters.

The present generation of commercially available multi-phase flow-meters measure these flow rates by using a combination of measurement techniques, such as Venturi, positive displacement, gamma-ray, X-ray, microwave and electrical impedance. These meters, however, are all in-line types which need to be placed inside the well tubular or, at least, need a window into the tubular to perform the measurements.

The invention also relates to a type of meter which is defined as "clamp-on" type of multi-phase flow-meter. Using this type of meter, there is no need to interfere with the integrity of the flow tubular onto which the meter is mounted.

Compared with the in-line meters, a clamp-on type multi-phase flow-meter offers strong operational and economic advantages:

The device is applicable to either periodic testing or permanent installation. It can be clamped on to the outside of a tubular with no disruption of production, small crew size, small equipment size, no production down-time for maintenance in the case of permanent installation. However, any sensor or combination of sensors in a clamp-on meter will have to measure the phase flow-rates through steel pipes, and this excludes many techniques used in in-line meters.

Techniques which are considered appropriate for clamp-on measurement include nuclear(gamma-ray, X-ray and neutron), acoustic and ultrasonic methods. Although at present, there are clamp-on type gamma-ray systems used for multi-phase flow metering, they form only part of a multi-phase flowmeter and need to be combined with other in-line type of measurements to produce the three flow-rates. Clamp-on passive acoustic sensors, in combination with other techniques, have been used to meter multi-phase flows.

In U.S. Pat. No. 5,415,048 a clamp-on acoustic system is described which, when used in combination with a differential pressure measurement system, produces the mass flow-rates of the liquid and gas phases. The complete system, however, does need pressure tapings on the pipeline, in order to take the differential pressure measurement. The other disadvantage of the passive acoustic measuring method is the poor signal to noise ratio at relatively low mass flow rates.

Ultrasonic clamp-on flowmeters are commercially available. Most of these are based on the transit time method, measuring upstream and downstream travel times of ultrasound pulses. An example are the meters made by Endress +Hauser Flowtec AG and described in U.S. Pat. No. 5,533, 408. The known meter combines a transit time measurement system with a cross-correlation system. The former is for clean fluids whereas the latter is for fluids containing foreign particles (reflectors). An automatic switch selects one or the other system depending upon the concentration of the reflectors.

The U.S. Pat. No. 4,735,097 shows a ultrasonic flow measurement system based employing a plurality of transducers located at two cross-sectional portions of a pipeline.

The U.S. Pat. No. 4,735,097 (or EP-A-0212470) and U.S. Pat. No. 4,838,127 describe the generation of surface waves in the pipe wall for clamp-on type ultrasonic flowmeters. It appears that the known flowmeters are using surface waves to increase the effective area of the source (and receiver). However, the flow itself is characterized by measuring the attenuation or travel time of longitudinal waves travelling through the liquid.

It is therefore an object of the invention to provide a flowmeter particularly suitable for monitoring streams of formation fluid as produced from subterranean hydrocarbon reservoirs.

SUMMARY OF THE INVENTION

The flowmeter of the present invention is based on measurements of the attenuation of various acoustic wave modes propagating in the pipe wall, in response to the presence of a fluid phase or mixtures of fluid phases in the pipe. Preferably, the flowmeter is designed for flows subject to gravity separation, i.e., non-vertical flows. It assumes an asymmetrical distribution of the phases in the flow.

Various wave modes can be excited in the pipe wall by appropriate setups of ultrasonic transducers mounted on the pipe periphery. These modes include those traveling along the axial direction, the circumferential direction and the radial or thickness direction of the pipe wall. The wave modes can be so-called bulk waves, i.e., compressional or shear wave modes, or various guided waves, in particular Lamb wave modes.

The bulk wave modes of interest to the present invention are those that are reflected between inside and outside surface of the pipe wall and hence travel in axial or circumferential direction along a zigzag path. The main radial mode is a compressional wave bouncing between the two surfaces of the pipe wall in the thickness direction, referred to as thickness mode reverberation in the wall. Lamb waves on the other hand are guided waves within the boundary of the two surfaces of the pipe wall. They are also referred to as "plate" waves and are sometimes classified as a subgroup of the so-called surface or Raleigh waves.

Many of the modes mentioned above, whether axial, circumferential or radial, are of leaky nature, i.e. they leak energy into the fluid phases, predominantly into any liquid phase present in the flow, that is in contact with the pipe wall. The amount of energy loss depends on the acoustic impedance of the liquid phase as well as on the fraction it occupies in the pipe, i.e. the liquid holdup. Therefore, by measuring the decay rates of appropriate wave modes in the pipe wall, the acoustic impedance and the holdup of the fluid phase/s can be determined. The appropriate wave modes are combined for the purpose of the present invention under the term "in-wall leaky acoustic wave modes".

In a multi-phase flow, the liquid holdup fluctuation causes fluctuations in the attenuation rate of the in-wall wave modes. These fluctuations provide tag signals (a characteristic temporal signature) of the flow. Therefore a time of flight measurement can be performed with two of such attenuation measuring channels arranged along the flow direction with known separation between them. A flow velocity can thus be obtained by combining the measured time delay and the separation.

Based on the above basic principle, the flowmeter comprises at least one but preferably two or more ultrasonic transmitter-receiver groups arranged on the outer surface of the pipe and with known separations between them. Each group comprises at least of one transmitter, which emits ultrasonic energy and generates axially, circumferentially propagating and/or radially reverberation wave modes in the pipe wall, and of at least one receiver, which detects the attenuation of the ultrasonic energy after propagating along the pipe wall for a given distance. The receiver can be implemented either by the same transducer that also functions as the transmitter or by one or more separate transducers mounted at different locations around the pipe periphery. Different combinations of the detected signals from one or multiple receivers can be utilized to obtain information on the holdup of the fluid phase/s and on distribution of the acoustic impedance in the pipe. As discussed below, there are various ways of measuring the acoustic impedance distribution and the liquid holdup.

The measurement of the fluid holdup can be combined with velocity measurements as obtained by the cross-correlation method to determine flow rates of individual phases. The accuracy of the measurements is determined by the wave mode, frequency, path geometry, combined with sufficient sensitivity to fluid impedance. Using the new method, information on fluid impedance can be readily generated through processing of the received signal.

Using axial Lamb waves with multiple transmitters and receivers, the fluid impedance distribution around the circumference of the pipe can be scanned. In a horizontal multi-phase flow with more or less stratified phase separation, this leads to the generation of a holdup distribution profile of the flow. This array of transmitter-receiver pairs serves as a multi-phase fraction meter.

When combined with the impedance cross-correlation and Doppler methods, a gas/oil/water three-phase flowmeter is produced. Alternatively, holdup profiles obtained from more than one of such arrays along the flow direction can be cross-correlated to produce a velocity profile. The combination of the holdup and velocity profiles produces the flow rates of individual phases.

The flowmeter in accordance with the invention operates as a non-intrusive device. It can be mounted as a clamp-on design or attached permanently to a flow tubular or pipe. In the field of production of hydrocarbons, its possible applications range from use as a surface testing device, over logging applications to permanent downhole flow monitoring by installation on a production tubing or by placing it into the space behind the casing.

Compared with the prior work on clamp-on cross-correlation flowmeters, the advantage of this invention is that the ultrasonic energy propagation path is in the pipe wall, rather than through the fluid. Therefore this method will work even at very high gas flow rates, where the other methods fail due to increased gas bubble concentration in the liquid phase, leading to the complete blockage of the through flow transmission. The applications are mainly aimed at horizontal pipes where the flow regimes are mainly slug/bubbly or wavy stratified. This invention, combined with an appropriate flow model, enables measurements of the flow rates of the individual phases in a multi-phase flow.

These and other features of the invention, preferred embodiments and variants thereof, and further advantages of the invention will become appreciated and understood by those skilled in the art from the detailed description and drawings following below.

EXAMPLE(S) FOR CARRYING OUT THE INVENTION

Figure 1:
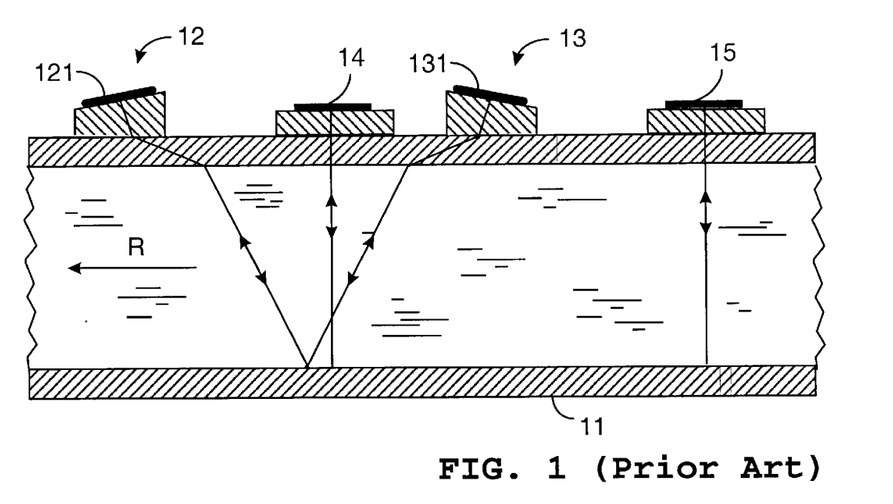
FIG. 1 is a schematic sectional view of the mechanical portion of a known clamp-on ultrasonic volumetric flowmeter.

Referring to FIG. 1, which is a highly schematic sectional view of the mechanical portion of a known clamp-on ultrasonic volumetric flowmeter as described in the Prior Art U.S. Pat. No. 5,533,408 mentioned above.

The known flowmeter comprises a first pair of ultrasonic transducers 12,13 disposed on the outside surface of a pipe 11 through which the fluid to be measured is flowing in the direction of arrow R. The ultrasonic transducers 12,13 are separated by a given distance in a direction parallel to the axis of the pipe.

A second pair of ultrasonic transducers 14,15, each of which is operated simultaneously as a transmitting transducer or a receiving transducer, are also disposed on the outside wall of the pipe so as to be separated by a given distance in a direction parallel to the axis of the pipe, but the angle between the direction of the ultrasound generated by them and the axis of the pipe is 90 degrees.

In the case of the first pair of ultrasonic transducers 12,13, this angle is different from 90 degrees since the transducers are wedge-shaped, with the apertures of the respective wedge angles facing toward each other. The wedge-shaped structure is achieved by providing a wedge of soundconducting material between the pipe 11 and the respective ultrasonic generator 121, 131.

As indicated in FIG. 1 by the ultrasonic beam shown, the wedge shape of the ultrasonic transducers 12,13 results in the ultrasound emitted by the ultrasonic transducer 12, for example, being incident on the inside surface of the pipe opposite the ultrasonic transducers 12,13 at an angle different from 90 degrees, and being reflected there to the ultrasonic transducer 13.

In the case of the ultrasonic transducers 14,15 of the second pair, the ultrasound propagates through the fluid in a direction virtually perpendicular and orthogonal to the direction of the axis of the pipe 11, and is reflected to the transmitting transducer at the opposite inside surface of the pipe.

Both pairs of transducer generate and receive ultrasonic signals that propagate through the fluid in the pipe and that are reflected once of the inside surface of the pipe opposite the transducers. The basic principle of the Prior Art device is to measure the attenuation of the wave as it propagates through the fluid or to measure the transit time difference between the waves traveling up-stream and down-stream through the fluid.

In contrast to the Prior Art example of FIG.1, the present invention exploits "leaky" wave modes propagating entirely within the pipe wall. While propagating within and along the pipe wall, the "leaky" wave modes lose (leak) energy to the fluid within the pipe through mode conversion and radiation at the boundary between the wall and the fluid. FIGS. 2A–D illustrate examples of these waves.

Figure 2A:
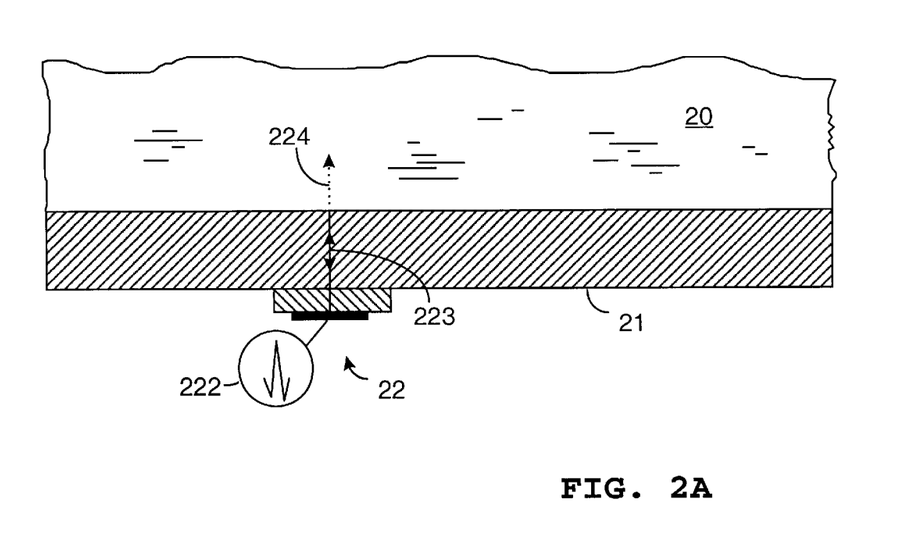
FIGS. 2A–D illustrate wave modes propagating through the pipe wall.

FIG. 2A illustrates a thickness reverberation mode. A transducer 22 attached to the outside surface of a pipe 21 emits a acoustic pulse 222 which in turn excites a thickness reverberation wave in the wall of the pipe 21. The wave is reflected back and forth between the inner and outer surfaces of the pipe wall. At each reflection at the inner surface, part of the wave energy is radiated (i.e. "leaks")into the fluid 20 flowing through the pipe. The travel path 223 of the reflected wave is indicated by solid arrows; a dashed arrow 224 indicates the propagation of the leaked part of the wave. Hence, the wave reflected at the inner surfaces looses part of its energy and appears at the transducer 22 with a reduced amplitude. The amount of the energy loss and hence the decay of the amplitude of the signal depends on the acoustic properties, particularly the acoustic impedance, of the fluid that is in contact with the inner surface of the pipe 21.

Figure 2B:
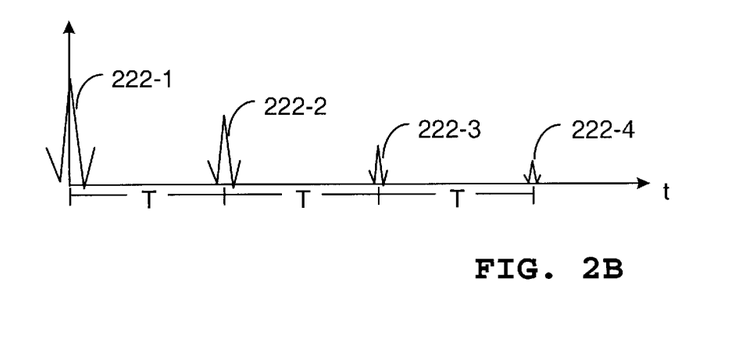

To facilitate the understanding of the leaky nature of this mode, a decay pattern of the signal 222 is shown in FIG. 2B.

Assuming the signal is emitted at zero time, a reverberation signal is received by the transducer 22 after multiples of time T where T is two times the wall thickness divided by the velocity of the wave (mode). As a result of the energy loss at the inner surface after each reflection, the amplitudes of the received signals 222-1,222-2,222-3,222-4 decay progressively.

Figure 2C:
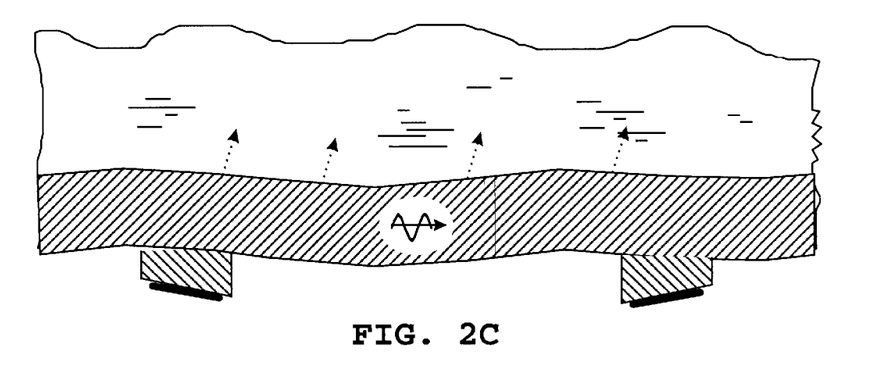
Figure 2D:
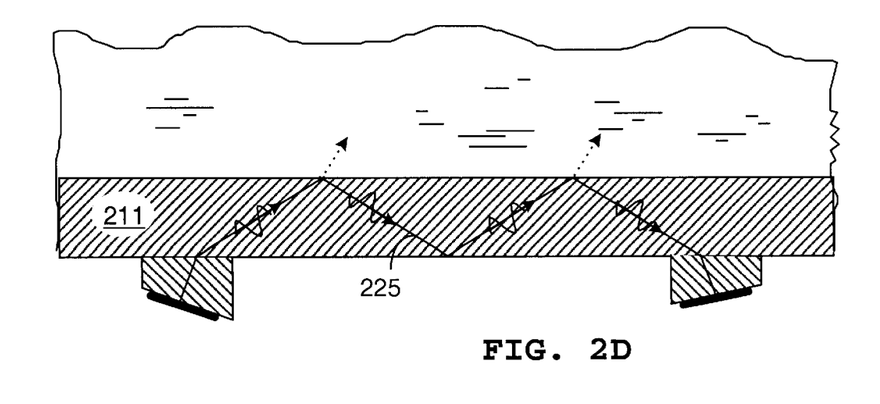

Other wave modes propagating through the wall of the pipe are illustrated by FIGS. 2C and 2D.

FIG. 2C depicts an asymmetric Lamb wave and FIG. 2D depicts an shear or compressional wave in a zigzag path 225 within the pipe wall 211. Again, solid arrows indicate the propagation direction of the wave while dashed arrows are used to indicate energy losses into the fluid flowing through the pipe.

The wave modes used by the invention travel through the wall of the pipe in either axial, radial or circumferential direction and any supposition of those directions. The transducers are positioned according to the intended measurement.

Figure 3A:
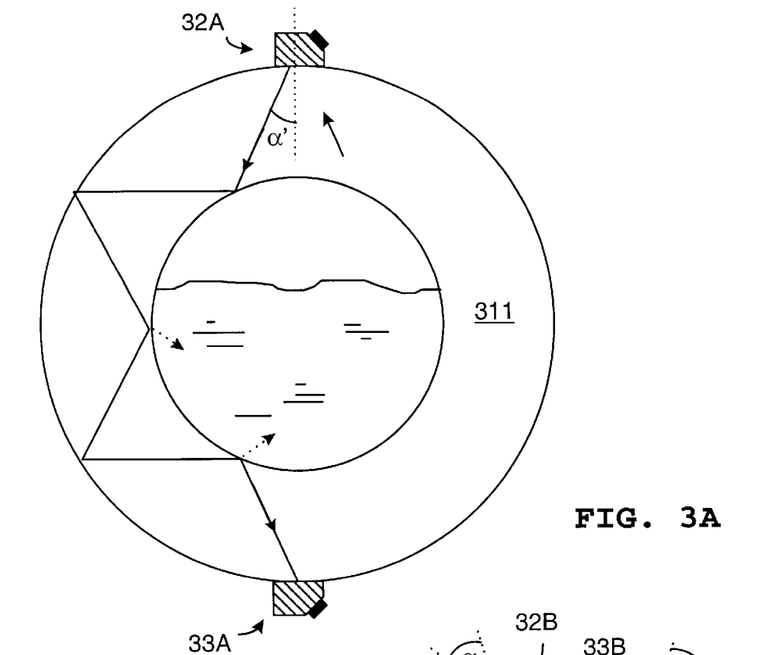
FIGS. 3A,B further illustrate flowmeters in accordance with the invention based on circumferentially traveling waves.
Figure 3B:
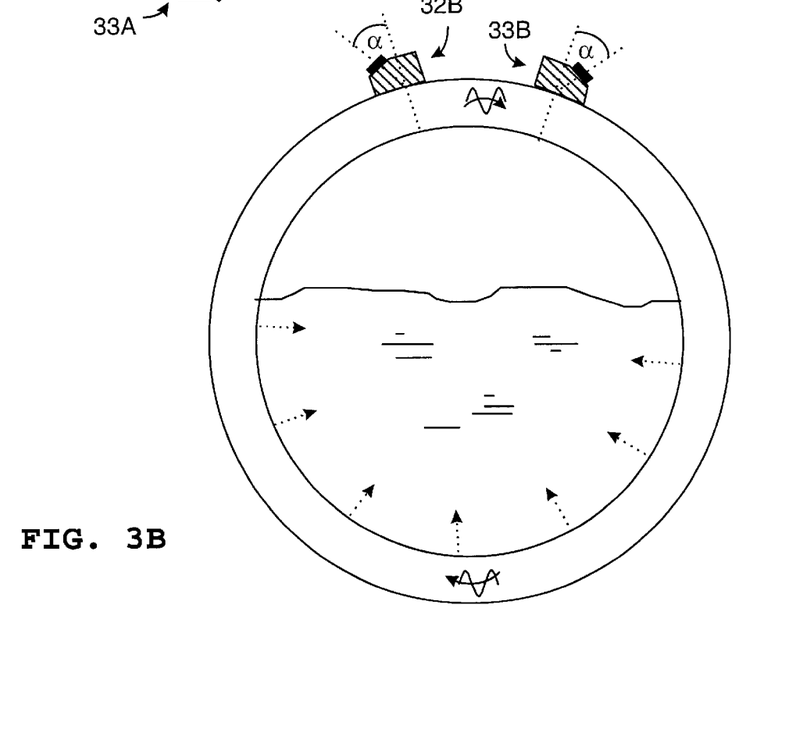

FIG. 3 illustrates two examples of circumferentially oriented transducers. FIG. 3A shows a flowmeter based on circumferentially propagating shear waves. FIG. 3B shows a flowmeter based on circumferentially propagating Lamb waves.

The cross sections 3A and 3B perpendicular to the axis of the pipe illustrates how wave energy is radiated into the liquid phase of the fluid. Above the gas/liquid interface the energy loss into the fluid becomes negligible.

The case of a circumferentially propagating shear wave is illustrated in FIG. 3A. The transmitter and receiver of each channel are mounted on opposite sides of the pipe. The angle of incidence α' is set to 38 degrees (hence the receiver is set to −38 degrees).

The case of a circumferentially propagating Lamb wave is illustrated in FIG. 3B. The transmitter and receiver of each channel are mounted facing each other and separated by a distance sufficient to let energy emitted by the transmitter develop fully into a Lamb wave before reaching the receiver location. The Lamb wave then completes its circular path within the pipe to be detected a second time by the receiver. A comparison between the received signal of the first and second arrival yields the total attenuation of the wave over the pipe's circumference. The angle of incidence α is set to 70 degrees (hence the receiver is set to −70 degrees). In general, the angle of incidence is chosen such that the refraction angle in the pipe wall is larger than the critical angle for shear waves and hence, a large fraction of the transmitted energy is converted into a Lamb type wave.

The type of the transmitter, i.e. compressional, shear or Lamb wave, and the angle of the incident beam into the pipe wall, α, can be selected so that different wave modes can be excited in the pipe wall. The typical value of α ranges from −90 degrees through 0 to +90 degrees, which enables the generation and detection of various compressional, shear and Lamb modes and different direction of travel (clockwise or anti-clockwise) for different application requirements.

The excitation waveform can be pulse, (short) tone-burst or continuous wave, although pulse is the preferred waveform used in the described examples for easy generation and detection.

Both FIGS., 3A and 3B, illustrate how, when the pipe is partly or fully filled with liquid, most of the propagating wave modes, referred to as leaky waves, leak energy into the liquid phase when traveling pass the section of the wall in contact with the liquid phase. Therefore the traveling waves are attenuated by the presence of the liquid phase in the pipe. For different wave modes, the expressions for the energy decay rate (also referred to as attenuation rate) in the pipe wall may be different and complex. For a given wave mode, however, the rate of attenuation, is a function of the acoustic impedance and the fraction (holdup) of the liquid phase in the pipe. For the shear wave of FIG. 3A, this is expressed in:

$$E = k_s \beta_s^x \qquad [1]$$

where $\beta_s$ is the shear wave reflection coefficient of the liquid/pipe-wall interface which is determined by the liquid acoustic impedance, x is a function of the holdup H which is related to the liquid/pipe-wall interface length which the shear wave has traveled through, and $k_s$ is a coefficient determined by the pipe geometries and the beam incidence angle. Both, $\beta_s$ and $k_s$, can be determined by calibration measurements on the empty and completely filled pipe. With both parameters known, the output of the receiver can be directly converted into a measure of x and, hence, into a measure of the holdup H.

For the Lamb wave of FIG. 3B, traveling around the pipe, the RMS value of the first wave arrival, $E_1$, at detector 1 should be higher than that of the second arrival, $E_2$, one cycle later, due to the attenuation effect. The ratio $E_2/E_1$, which represents the attenuation rate can be approximately expressed by:

$$E_2/E_1 = k_L \beta_L^x, \quad [2]$$

where $k_L$ is a coefficient related to the wave decay in the empty pipe and $\beta_L$ is the attenuation coefficient related to the acoustic impedance of the liquid.

Based on the principles of leaky wave modes described above, the device illustrated by FIG. 4 shows two clamp-on ultrasonic measurement channels. The channels are axially separated by a distance d of 160 mm equal to one pipe diameter (usually chosen to lie within 1 to 10 times of the pipe diameter). Each of the channels consists of one transceiver 42, 44, and one receiver R 43, 45. Transmitters (and receivers) operate at 0.5 MHz.

Figure 4:
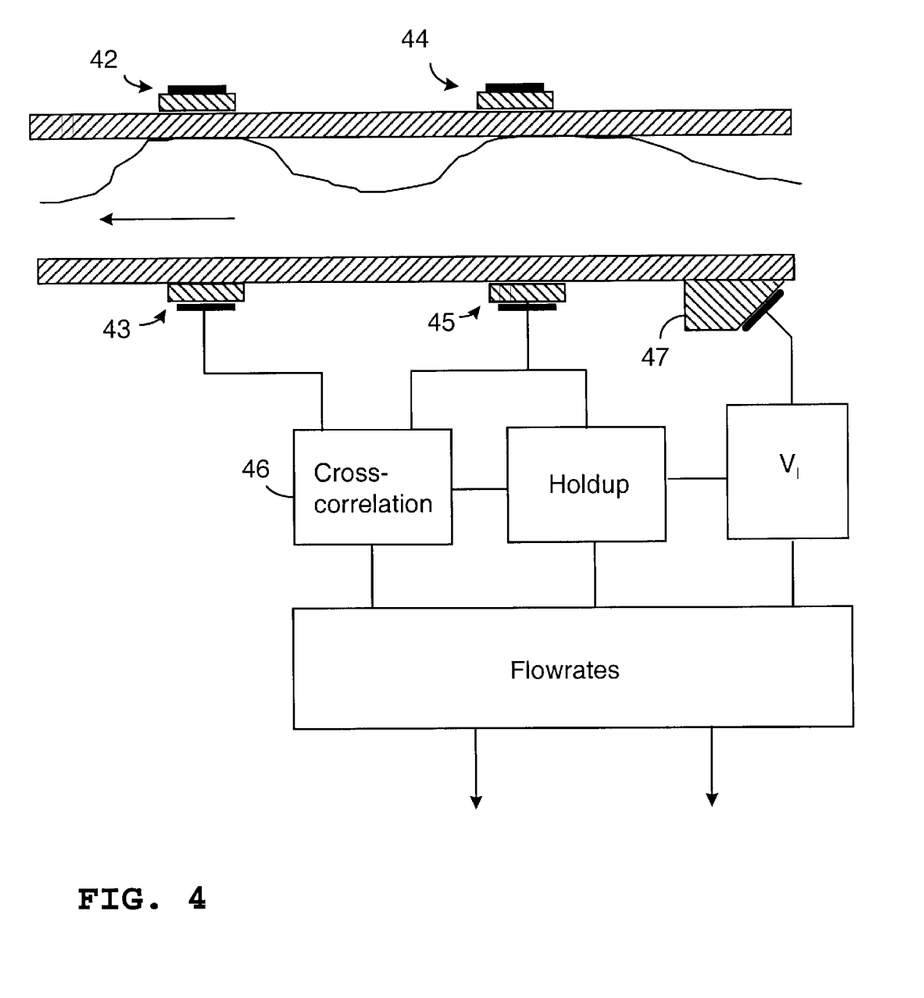
FIG. 4 shows a more detailed diagram of a flowmeter in accordance with an example of the invention.

A cross-correlator 46 produces a time-of-flight measurement using the measurements of the dynamic fluctuations of the energy attenuation at the two channels. The known separation, d, which is in the examples described 160 mm, and the measured time delay, τ, are then substituted into the following equation to calculate the flow velocity:

$$V_f = d/\tau \quad [3]$$

This measured velocity, $V_f$, can be interpreted by using appropriate flow models to produce the mixture or homogeneous velocity of the flow, $V_h$. Appropriate flow models are known. Examples are published by Dukler, A. E. and Hubbard, M. G., in: "A model for gas liquid slug flow in horizontal and near horizontal tubes", Ind. Eng. Chem. Fundam. 14(1975), 337–347 and by Nicholson, M. K., Aziz, K. and Gregory, G. A., in: "Intermittent two phase flow in horizontal pipes: predictive models", Can. J. Chem. Eng. 56(1978), 653–663.

A Doppler sensor 47, which is typically an angled shear wave probe, is mounted on the bottom side of the pipe. For some application, it can be advantageous to add a second Doppler probe on the top side of the pipe. Doppler frequency shifts produced by gas bubbles and solids particles in the liquid phase provide information on the velocity of the liquid phase, $V_l$.

Flow rates of individual phases can be derived from above three measurements using the following equations:

$$Q_l = AH_l V_l \quad [4]$$

and $$Q_g = A(V_h - H_l V_l) \quad [5]$$

where A is the cross-sectional area of the pipe bore.

Alternatively, the two measured parameters, $V_l$ and $H_l$ can be combined with a slip model to give $Q_l$ and $Q_g$. The slip model provides the differential or slip velocity $V_s$ between the liquid and the gas, and, hence, enables the gas velocity $V_g$ to be determined from the following relationship:

$$V_g = V_s + V_l \quad [6]$$

where $V_s$ is the slip velocity. The flow rate for the gas flow can then be determined by replacing equation [5] with $$Q_g = A(1 - H_l)V_g \quad [7]$$

Figure 5A:
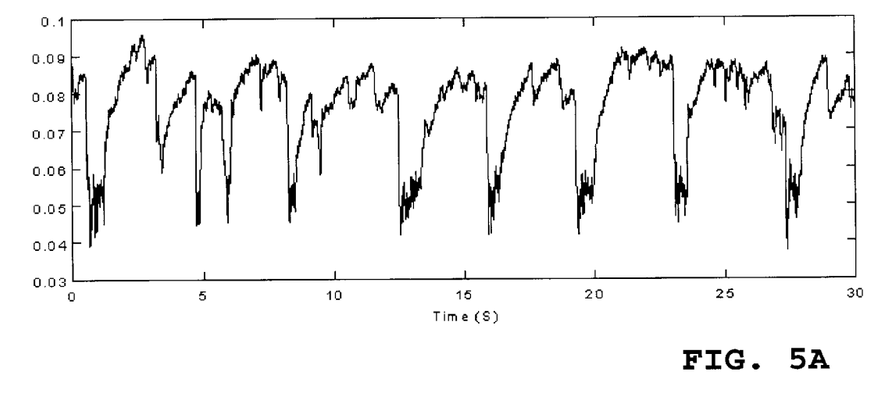
FIGS. 5A,B show attenuation signals as measured by a flowmeter in accordance with an example of the invention.
Figure 5B:
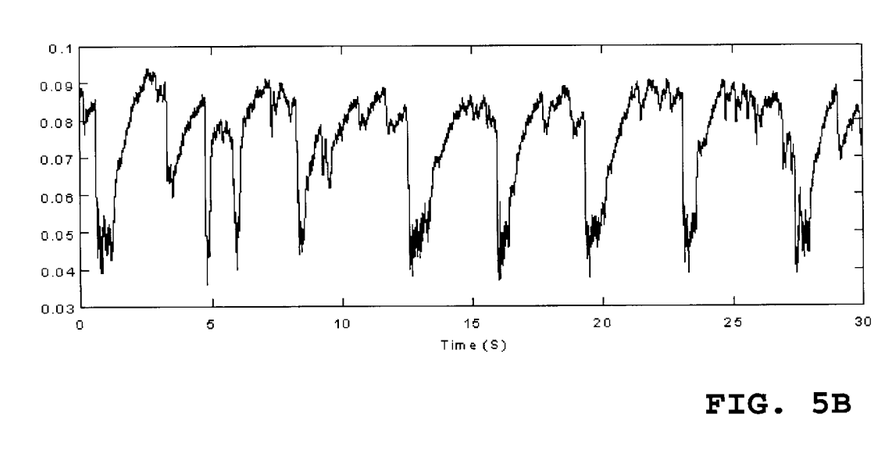

FIGS. 5A,B show the attenuation signals from the two transmitter-receiver channels, respectively. The three-phase flow consists of a liquid flow rate of 20 m³/hour (10 m³/hour oil mixed 10 m³/hour water) and a gas flow rate of 50 m³/hour. The peak value of cross-correlation between the up and down-stream sensing channels gives the time delay. The velocity of the flow is determined from equation [3] using this time delay.

Figure 6:
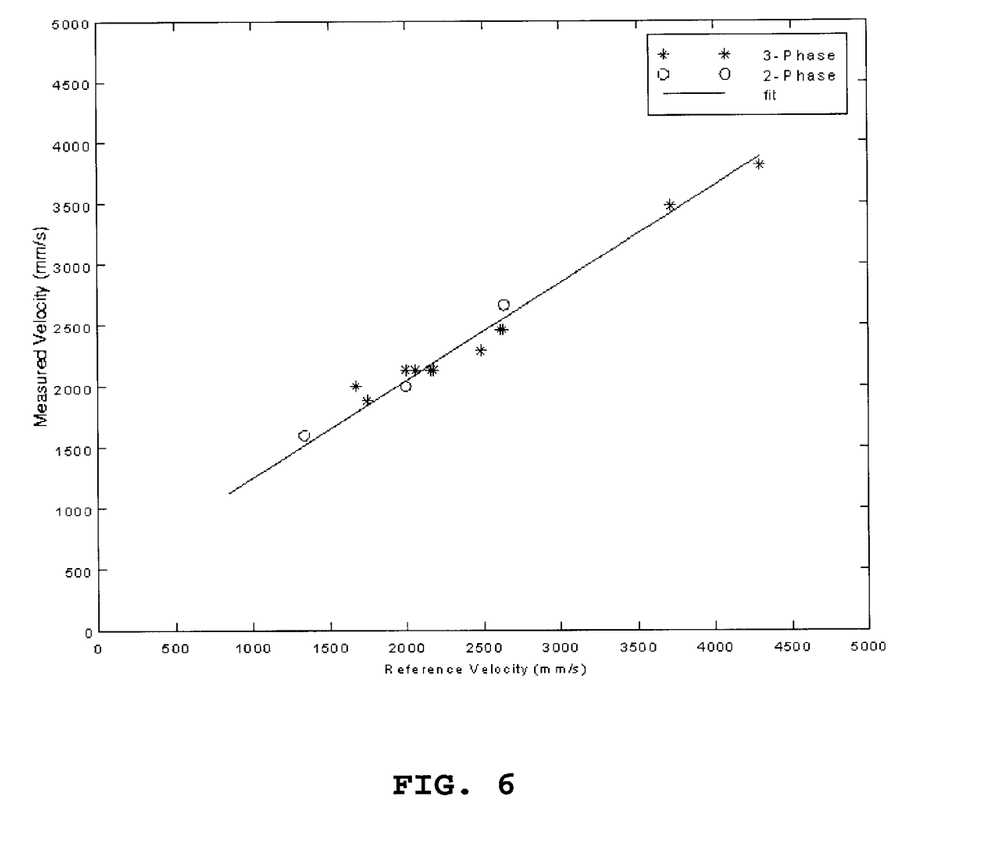
FIG. 6 depicts velocities obtained by a flowmeter in accordance with an example of the invention in comparison with reference velocities.

FIG. 6 shows the cross-correlation velocities obtained using this method versus reference homogeneous velocities for various two-phase and three-phase oil/water and oil/water/gas flows. The solid straight line shows the fitted calibration line.

Figure 7:
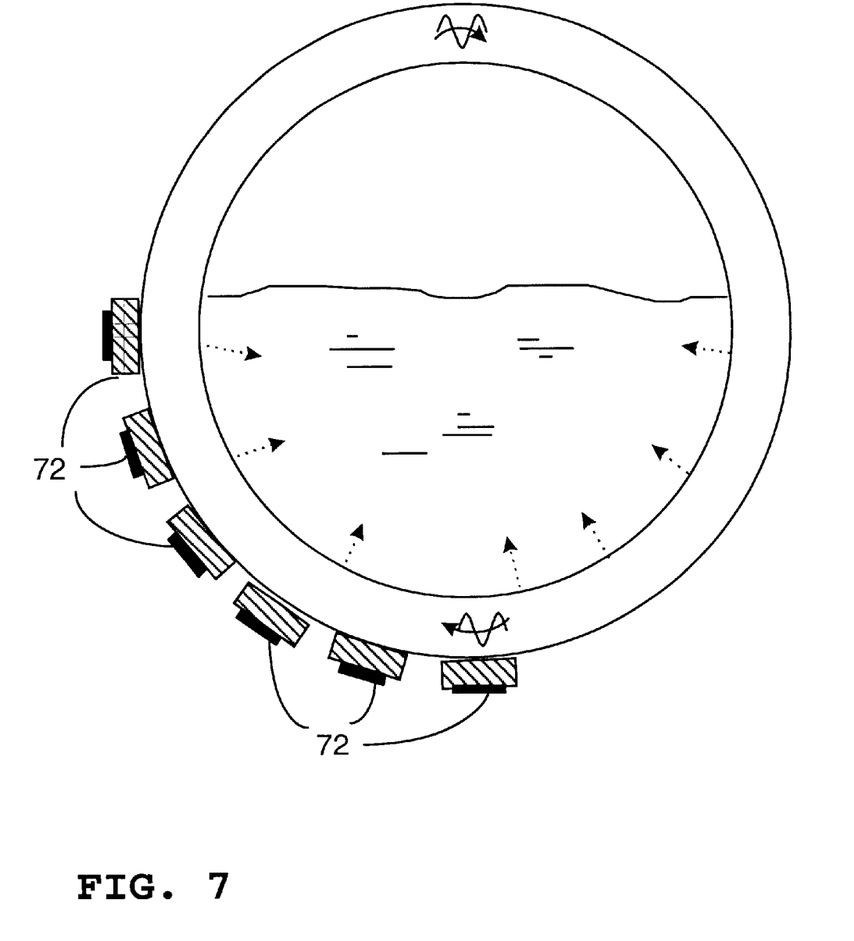
FIG. 7 illustrates a further example of a flowmeter based on circumferentially traveling waves.

Other methods of exciting specific type of wave modes include the use of an array 72 of transmitters as shown in FIG. 7, where the phase and amplitude of the voltage waveforms applied to transducer elements and the inter-element separations can be selected according the pipe geometries to generate and detect Lamb wave modes in the pipe wall.

Figure 8A:
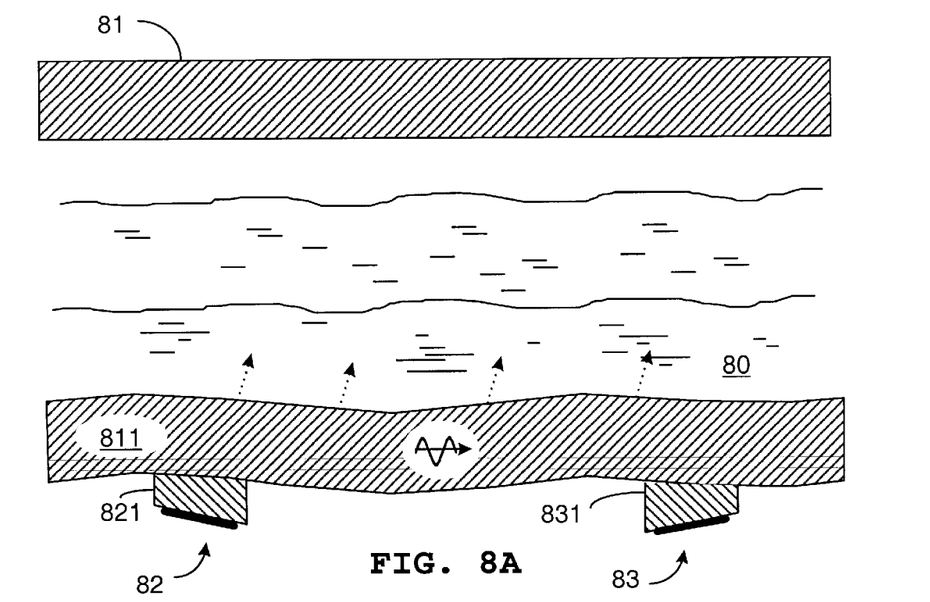
FIGS. 8A,B illustrate examples of flowmeters based on axially traveling Lamb waves.
Figure 8B:
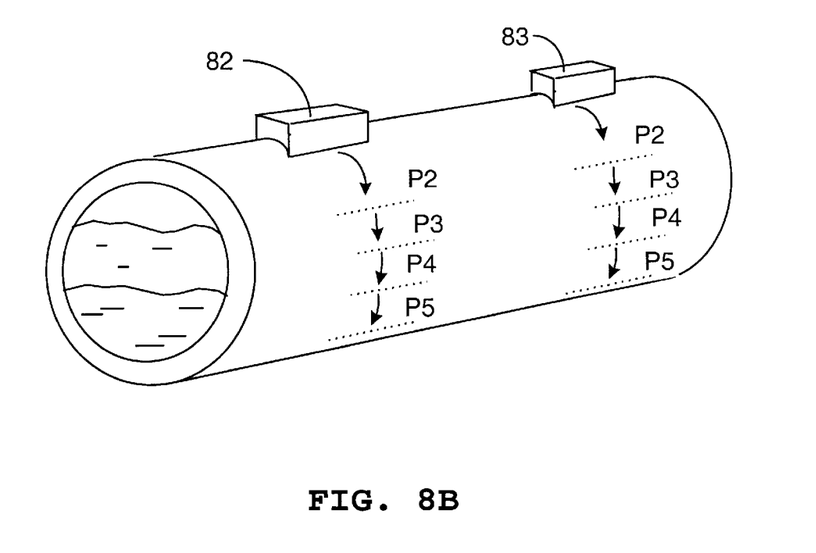

The basic principle of another example of the invention is to generate one or several axially traveling Lamb wave modes in the pipe wall and measure the wave attenuation over a given distance. FIGS. 8A and 8B illustrate a typical implementation of such a system. An ultrasonic transmitter 82 and a receiver 83 are mounted along the axial direction of the pipe 81, separated by a given distance. The transmitter 82 emits ultrasonic energy of suitable form into the pipe wall 811 so that an appropriate Lamb wave mode is generated in the pipe wall, propagating along the axial direction towards the receiver 83. The selected Lamb wave is one of the leaky modes which leak energy into the liquid 80 that is in contact with the pipe wall 811. The transmitter and receiver are both V101 1-inch 0.5 MHz wideband transducers from Panametrics. These are coupled to a section of a steel pipe via two PVC wedges 821, 831 providing 70 degree incidence angle. This setup satisfies the post shear critical incidence angle (about 60 degrees) so that only a single flexural wave mode is generated.

The length of the average wave path in the pipe wall, L, is about 200 mm. The steel pipe is partially filled with tap water and oil (kerosene), forming a three layer stratified distribution of air, oil and water.

Some of the leaked energy may be reflected back to the pipe wall by flat interfaces between the fluid phases, generating the so-called third interface echo (TID). However, the TID arrives at the receiver later than the direct Lamb wave. Therefore an appropriate time window can be chosen to ensure the detection of only the direct arrival.

The amplitude of the direct Lamb wave arrival gives an indication of the liquid property along the wave path. The energy of this arrival can be expressed by the following equation:

$$E = k 10^{\beta L} \quad [8]$$

where L is the separation (as measured along the perimeter of the pipe) between the transmitter and the receiver, β is the attenuation coefficient due to the fluid inside the pipe. For a given wave mode and frequency, β is a function of the acoustic impedance of the fluid(s) in the pipe. The coefficient β is measured in decibel/meter. The coefficient k is a determined by factors such as the emitting power of the transmitter, the coupling material between transducers and the pipe, the pipe geometry etc. It can be determined through a calibration procedure. For instance, the system can be calibrated when the pipe is empty, in which case E equals k. Defining $$\delta = 10\log\frac{E}{E_e} = 10\beta L, \qquad [9]$$

where δ is the attenuation ratio in decibels and $E_e(=k)$ is the calibration on the empty pipe.

Since in most cases β is proportional to z, the acoustic impedance of the fluid, the sensitivity of the impedance measurement can be obtained by differentiating eq. [8] to $$\frac{d\delta}{dz} \propto 10L. \qquad [10]$$

The sensitivity of the measurement to changes in the attenuation coefficient is a function of length L. In practice an appropriate L value should be chosen to satisfy both the required sensitivity and the required spatial resolution along the axial direction of the flow.

In the experiment as illustrated in FIG. 8B, the transmitter-receiver pair 82,83 was first located in a position as shown where only air is in contact with the inside of pipe wall. The transmitter-receiver was then moved to other positions as marked in the figure. In position P2, the center of the transducer was close to the air/oil interface. In position P3, the wave path was entirely in contact with oil. In position P4, the center of the wave path was close to the oil/water interface and finally in position P5, the wave path was entirely in contact with water.

The received signal is in a compact waveform indicating the single mode nature of the Lamb wave. The center frequency of the signal is around 250 kHz. The amplitude of the wave decreases as the wave path moves from low impedance near 0 Mrayl=0 $10^6$ kg/(m$^2$s) for air through the interfaces to higher impedances (oil 1.05 MRayl and water 1.5 MRayl).

The amplitude of each of the signals is measured and squared to produce the peak power value. All the values are normalized by that corresponding to air. Then a log operation such as that shown by equation [9] is applied to produce an attenuation value in decibel. The attenuation values for the five test positions show a difference in attenuation of more than 2 dB between oil and water for this specific setup. The sensitivity may be further increased by optimizing the design of the setup to select more appropriate mode and frequency combinations.

The selection of suitable mode and frequency is very important for an application such as water liquid ratio measurement. There are many possibilities selecting an wave mode. In order to simplify interpretation, generation and detection, a single mode, such as one of the flexural modes, is often a sensible option. There may also be advantages in using several distinct (easily distinguishable in time domain due to different velocities) modes which have different frequencies and possibly different sensitivities to different liquid properties. Non-leaky modes may also be generated in order to detect pipe defects and to calibrate transducer sensitivity and quality of coupling to the pipe. In cases where L is large, the frequency should be selected around the minimum dispersion and minimum loss points on the Lamb wave dispersion curves, in order to maintain a compact waveform of the chosen mode.

The transmitters and receivers for the Lamb wave generation and detection may be angled transducers with liquid or solid coupling to the pipe, or transducer arrays such as the flexible inter-digital transducers by P. Cawley et al. in Ultrasonics, 35, 489–498 (1997). A receiver may also be replaced with an appropriate reflector so that the same transducer or transducer array can used as both the transmitter and the receiver.

In order to determine the phase holdups in a three-phase flow, the acoustic properties of oil and water must be known. Provided that the pipe can be filled in turn with 100 per cent water, oil and gas samples, three calibration points can be obtained following equations:

$$E_{water} = k10^{\beta_{water}L} \qquad [11]$$

$$E_{oil} = k10^{\beta_{oil}L} \qquad [12]$$

$$E_{gas} = k10^{\beta_{gas}L} \qquad [13]$$

where L is the path length of the axially traveling Lamb wave.

By dividing equations [11] and [12] with [13], and taking the attenuation in decibel, attenuation ratios of water and oil can be found as $$\delta_{water} = 10\log\frac{E_{water}}{E_{gas}} = 10\beta_{water}L \qquad [14]$$

and $$\delta_{oil} = 10\log\frac{E_{oil}}{E_{gas}} = 10\beta_{oil}L \qquad [15]$$

The assumption of $\beta_{gas}=0$ is used to derive equations [14] and [15]. In case of a water oil mixture, the water liquid ratio can be obtained from the measured $\delta_1$ through an interpolation between the two 100% calibration points, $\delta_{oil}$ and $\delta_{water}$.

FIG. 8B shows that by placing axial Lamb wave transceivers along the circumference of the pipe it is possible to generate holdup information of a multi-phase flow. In order to measure the phase holdups in flows with asymmetrical phase distribution, such as those in a horizontal pipe, the axially traveling Lamb wave measurement described above should be performed around the entire circumference of the pipe, or at least around half of the circle if the phase distribution is symmetrical about the vertical diameter of the pipe.

Figure 9:
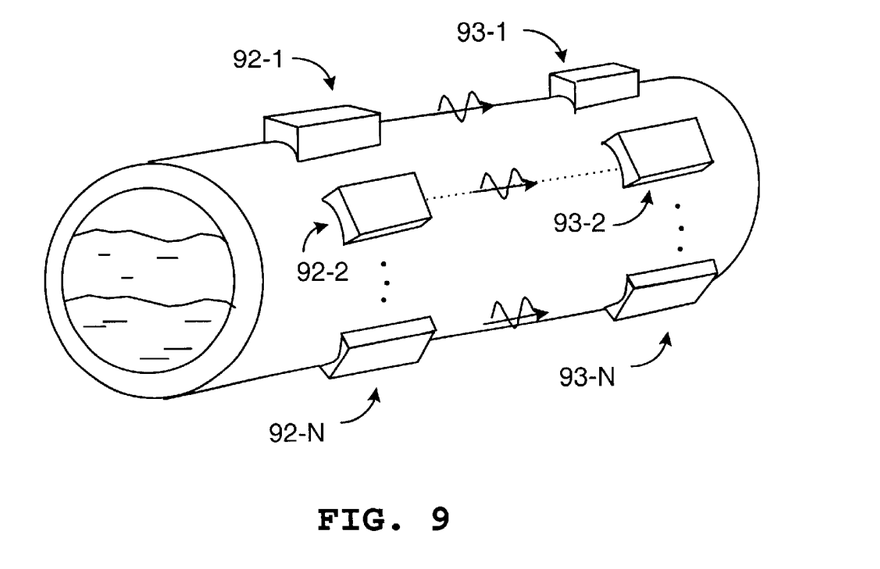
FIG. 9 illustrates a further example of a flowmeter based on axially traveling Lamb waves.

FIG. 9 shows a possible implementation of such a system. A number of N transmitter-receiver pairs 92-1,93-1,92-2, 93-2,92-N, 93-N are used to form N parallel axially traveling Lamb waves around the circumference of the pipe. The gaps between the pairs do not need to be equally spaced. For instance on a horizontal pipe, more transducers can be placed near the middle and less on the top and under side of the pipe in order to compensate the lack of holdup resolution around the middle positions. If the flow is symmetrical about the vertical diameter of the pipe, the transducers on one side of the diameter can be mounted on vertical heights which are different from those of the other side. Therefore the combination of the two sides can provide twice as many measurement positions as those provided by a symmetrically mounted transducer array.

With the system shown in FIG. 9, an impedance or holdup profile of the flow can be constructed by mapping each of the attenuation measurements onto its corresponding position on the pipe periphery. The holdup of water, oil and gas can be calculated from this profile. If more than one such systems are installed on the pipe along the flow direction. Holdup profiles from upstream and downstream positions can be cross-correlated to produce velocity information.

Since the dynamic changes of the holdup profiles are caused mainly by the variations of large interface positions, such as those of gas/liquid and oil/water, cross-correlation tends to give these interface velocities. With appropriate flow model, these can be interpreted to give the velocities of all the three phases. Additional velocity information can be obtained using techniques such as the pulsed Doppler velocimetry. Combining the holdup profile with the velocity information leads to a multi-phase flowmeter, providing the flow rates of all the individual phases.

The setup shown in FIG. 9 can be further extended to include multiple receivers along the axial direction with known separation between them.

Figure 10:
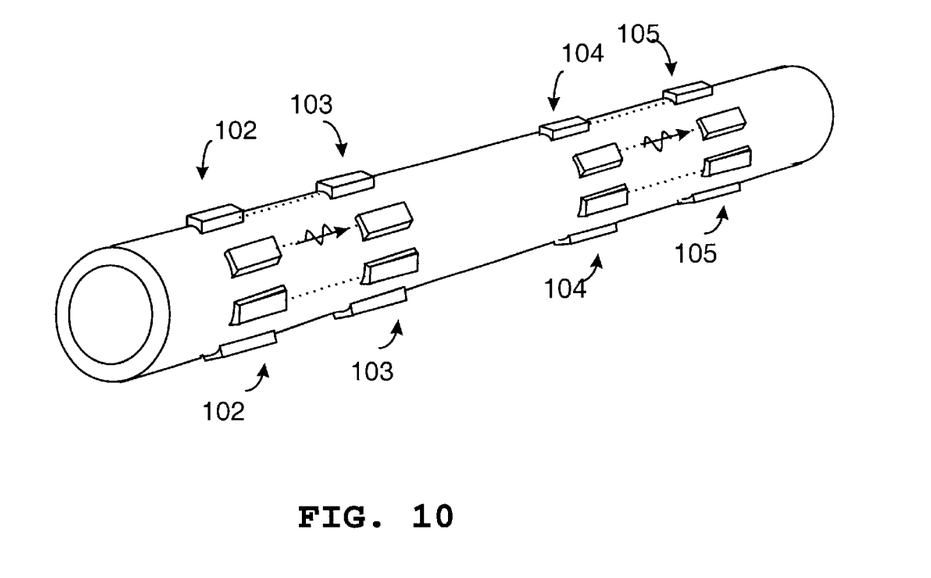
FIG. 10 illustrates a further example of a flowmeters based on axially traveling Lamb waves.

FIG. 10 shows such a variant of the invention comprising in addition to the transmitter-receiver pairs 102,103 as shown in FIG. 9 multiple receiver lines 104,105 positioned in parallel with the first line of receivers. The attenuation of the Lamb wave between any two receiving points can be measured and this enables a holdup profile along the axial direction to be obtained.

Combining measurements in circumferential and axial direction of the pipe as shown for example in FIGS. 9 and 4, respectively, produces a 2-D (horizontal and vertical) distribution map of the phases. This provides more information on the flow regime and thus leads to better flow modeling and more accurate holdup and velocity measurements. Where the required axial mapping distance exceeds the traveling distance of the Lamb wave generated by the transmitter, due to the decay of the wave, multiple transmitter-receiver pairs (or single transmitter multi-receivers) can be arranged along the axial direction to extend the coverage range as shown in FIG. 10.

Figure 11A:
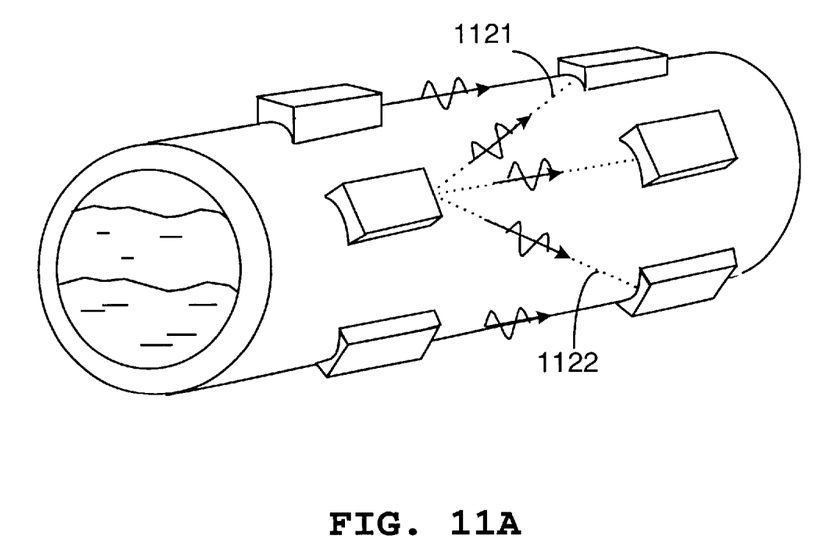
FIGS 11A,B show examples of flowmeters using crosstalk between transmitter and receivers.
Figure 11B:
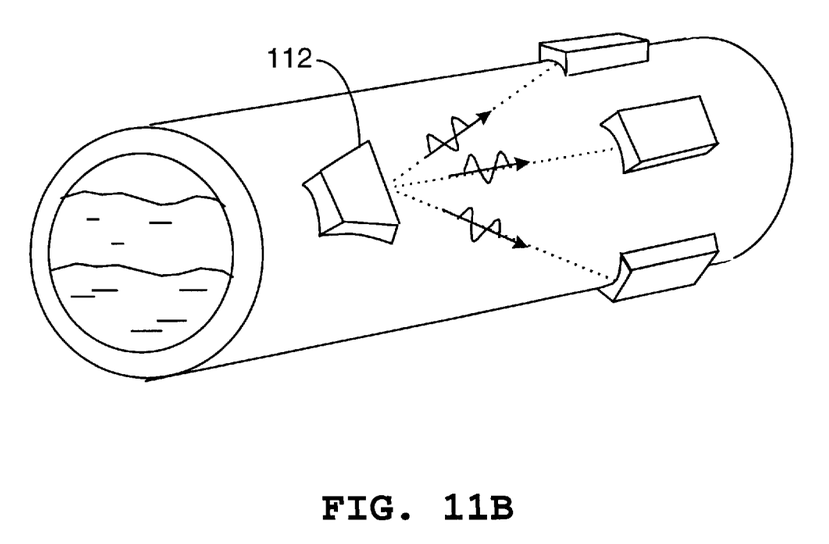

Other possible extensions of the principle include the utilization of the cross-talk waves, i.e. waves from one transmitter to the receivers that are not at the same circumferential position. An example of cross-talk waves is illustrated in FIG. 11A. Attenuation along the diagonal or cross-talk paths 1121 and 1122 can be measured and a tomographic reconstruction can be performed to obtain the phase distribution profile. As FIG 11B illustrates, such diagonal Lamb waves can also be generated and detected intentionally using fan-shaped transducers 112 as transmitters and/or receivers.

Figure 12:
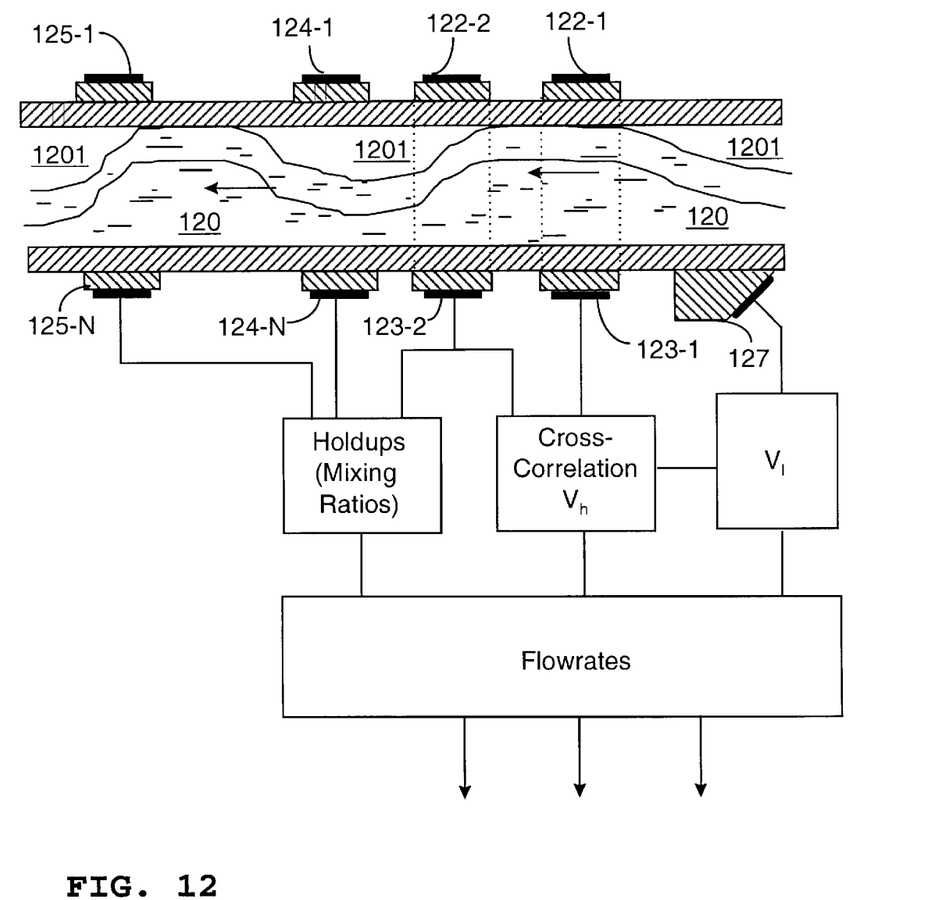
FIG. 12 shows a more detailed diagram of a flowmeter in accordance with an example of the invention combining measurements of axially and circumferentially traveling waves.

An ultrasonic clamp-on flowmeter combining an axial wave (i.e. Lamb wave) system with circumferential wave system is schematically depicted in FIG. 12.

The flowmeter is attached to a pipe. The fluid 120 flowing through the pipe has a liquid component and a gas component. At certain gas-liquid flow ratios, the liquid flows in slugs separated by larger gas bubbles 1201. The flowmeter comprises three systems: a circumferential Lamb wave system comprising two transmitter/receiver combinations 122-1,122-2,123-1, 123-2, an axial Lamb wave system 124-1,124-N,125-1,125-N and a Doppler based velocity meter 127.

The outputs or measurements of the two Lamb wave based systems are combined to generate a holdup profile of the flow. Using further the simplifying assumption that the velocity of the two liquid phases are equal, the flow rates $Q_w$, $Q_o$ and $Q_g$ for water, oil and gas, respectively, can be calculated.

The flowmeter can be refined by adding further systems to it, such as mounting a second Doppler system in proximity to the top of the pipe in order to measure the velocity of slugs in the flow or by using a (gamma-ray based) density measurement system to determine for example an average holdup.

What is claimed is:

1. An apparatus for measuring one or more parameters related to a fluid flowing in a conduit, the apparatus comprising:
    at least one transmitter to generate acoustic waves;
    at least one receiver to receive acoustic energy, the at least one transmitter and at least one receiver being mounted on an outside surface of the conduit; and
    additional electronic components wherein the transmitter is positioned and directed so as to generate at least one in-wall leaky acoustic wave mode and said receiver is positioned and directed and electronic components are adapted so as to receive and to determine the attenuation of waves having said mode and having propagated entirely within the wall of the conduit from the transmitter to receiver, and wherein at least some of said attenuation is caused by leaking of acoustic energy out of the wall of the conduit into fluid flowing inside the conduit, and wherein said one or more parameters related to the fluid flowing in the conduit are derived at least in part from said attenuation.

2. The apparatus of claim 1, wherein the receiver and electronic components are arranged to determine the attenuation of waves caused by an impedance mismatch at the boundary between fluid and pipe wall.

3. The apparatus of claim 1 having a clamp-on section to provide a releasable connection between said at least one transmitter and at least one receiver on the one hand, and the wall of the conduit on the other hand.

4. The apparatus of claim 1 having at least one pair of transducers configured as transmitter and receiver located at essentially the same position as measured along a direction parallel to the central axis of the conduit to generate and receive in-wall leaky acoustic wave signals traveling in essentially circumferential direction.

5. The apparatus of claim 1 having at least one pair of transducers configured as transmitter and receiver located at essentially in a line parallel to the central axis of the conduit to generate and receive in-wall leaky acoustic wave signals traveling in essentially axial direction.

6. The apparatus of claim 1 having a plurality of pairs of transducers configured as transmitters and receivers to generate and receive in-wall leaky acoustic wave signals traveling in an essentially axial direction, each of the transmitters being located on the surface of the conduit at essentially a first axial position and each of the receivers being located on the surface of the conduit at essentially a second axial position.

7. The apparatus of claim 1 having at least one pair of transducers configured as transmitter and receiver to generate and receive in-wall leaky acoustic wave signals traveling in essentially circumferential direction and at least one pair of transducers configured as transmitter and receiver to generate and receive in-wall leaky acoustic wave signals traveling in essentially axial direction.

8. The apparatus of claim 1 having a first arrangement of transducers to generate and receive in-wall leaky acoustic wave signals, a second arrangement of transducers to generate and receive in-wall leaky acoustic wave signals, and a cross-correlator connected to said first and second arrangement.

9. The apparatus of claim 1 having at least one receiver for receiving in-wall leaky acoustic wave signals generated by at least one transducer located at a position both axially and circumferentially separated from the position of said at least one receiver.

10. The apparatus of claim 1 in combination with a Doppler based velocity meter.

11. The apparatus of claim 1 in combination with a Gamma-ray based density meter.

12. Method of measuring parameters characteristic of a fluid flow in a conduit, comprising the steps of engaging at least one transducer to generate acoustic waves and at least one transducer to receive acoustic energy with an outside surface of a conduit carrying the fluid to be measured;

generating and receiving signals representing at least one in-wall leaky acoustic wave mode;

evaluating the attenuation of the at least one wave mode that has entirely propagated within the wall of the conduit from the generating to the receiving transducer, wherein at least some of said attenuation is caused by leaking of acoustic energy out of the wall of the conduit into fluid flowing inside the conduit; and deriving at least one of said parameters characteristic of the fluid flow in the conduit at least in party by using the result of said step of evaluating.

13. The method of claim 12 wherein the flow comprises at least two phases.

14. The method of claim 13 comprising the steps of generating and receiving signals representing in-wall leaky acoustic wave modes traveling in essentially circumferential direction; and evaluating the attenuation said signals to derive a parameter representing a phase holdup.

15. The method of claim 13 comprising the steps of generating and receiving a plurality signals representing in-wall leaky acoustic wave modes traveling in essentially axial direction at different circumferential positions; and evaluating the attenuation said signals to derive a parameter representing a phase holdup.

16. The method of claim 12 comprising the steps of engaging at least two arrays each comprising at least one transducer to generate acoustic waves and at least one transducer to receive acoustic energy with the outside surface of the conduit at different axial positions;

generating and receiving signals representing in-wall leaky acoustic wave modes; and cross-correlating said signals or signals derived therefrom to calculate a velocity.

17. The method of claim 16 further comprising the step of combining the velocity measurements and a holdup measurement to calculate flow rates of different phases within the fluid.

18. The method of claim 12 comprising the steps of engaging a plurality of transducer pairs with the conduit, each pair being either axially or circumferentially separated, and using the measured attenuation of wave modes to derive a two dimensional map of a phase distribution within the fluid.

19. The method of claim 12, using cross-talk measurements between transducers at different axial and circumferential positions to determine a tomographic reconstruction of a phase distribution within the fluid.

* * * * *